United States Patent [19]

Drewlow

[11] Patent Number: Plant 7,260

[45] Date of Patent: Jul. 3, 1990

[54] BEGONIA PLANT NAMED DESIRÉ

[75] Inventor: Lyndon W. Drewlow, Ashtabula, Ohio

[73] Assignee: Mikkelsens, Inc., Ashtabula, Ohio

[21] Appl. No.: 360,426

[22] Filed: Jun. 2, 1989

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Begonia plant named Desiré having double flowers orange in color, relatively large flower diameter, red pigmentation on upper and lower leaf surfaces, early flowers, tepal margin entire, long lasting flowers, and an ability to be propagated by stem or leaf cuttings.

1 Drawing Sheet

The present invention relates to a new and distinctive cultivar of Begonia plant, botanically known as *Begonia hiemalis*×*Begonia fotsch,* and known by the cultivar name Desiré.

The new cultivar was discovered by me as a seedling from a controlled crossing of Tuberous Begonia Mikkelsen seedling 84-628-16, as the seed parent with *B. socotrana* Mikkelsen seedling 85-1016-3 as the pollen parent.

Asexual reproduction by both stem and leaf cuttings has reproduced the unique features of the new cultivar through successive propagations.

The following characteristics distinguish the new begonia from both its parents and other begonias commercially known and used in the floriculture industry. In the comparison, specific references are made to previously patented cultivars, including St. Helena (U.S. Plant Pat. No. 6,329), Schwabenland Improved Orange (U.S. Plant Pat. No. 3,723), and Aphrodite Cherry Red (U.S. Plant Pat. No. 3,319).

1. Desiré has orange flowers which are brighter in color than the lighter orange St. Helena and have more red pigmentation that the orange flowered Lido (not patented) and Schwabenland Improved Orange.

2. Flower size is larger than any of the comparison cultivars, including the hanging basket type Aphrodite Cherry Red.

3. Desiré is not double flowered as St. Helena but is more double than Aphrodite Cherry Red, the semi-double Lido, and the single Schwabenland Improved Orange.

4. Desiré is not as pendulous as Aphrodite Cherry Red but more pendulous in growth than the upright growing St. Helena, Lido and Schwabenland Improved Orange.

5. Stem diameter is greater than Aphrodite Cherry Red, similar to St. Helena, but not as great as Lido and Schwabenland Improved Orange.

6. Desiré has the most red pigmentation on lower and upper mature leaf surfaces. St. Helena has red pigmentation only on the lower surface, and Aphrodite Cherry Red, Lido and Schwabenland Improved Orange have no red pigmentation. Desiré has the deepest reddish green leaf of the comparison cultivars.

7. Desiré has rounded leaves similar in size and shape to St. Helena and Schwabenland Improved Orange, with Lido having a more pointed and slightly smaller leaf with more serration on the margin; Aphrodite Cherry Red has the smallest leaf but margin and shape are similar to Desiré.

8. Desiré has an average of 3 flowers per raceme, which is similar to Lido and Schwabenland Improved Orange, while Aphrodite Cherry Red and St. Helena have 4 to 5 flowers per raceme.

9. Desiré has the heaviest red pigmentation in the stems and petioles on mature plants, followed by St. Helena, then Lido, with Aphrodite Cherry Red and Schwabenland Improved Orange having red pigmentation mainly at the nodal area.

10. Desiré has a slight overlap of lower leaf nodes like St. Helena and Lido, with Schwabenland Improved Orange being more overlapped and Aphrodite Cherry Red having no overlap.

11. Desiré has an entire tepal margin like Schwabenland Improved Orange and Aphrodite Cherry Red, with Lido and St. Helena having a more serrated tepal margin.

12. Will flower under long day conditions and is early flowering.

13. Propagates readily from both stem and leaf cuttings and breaks well from pinch.

14. Flowers are long lasting, do not shatter when shipped, and are very large in size.

15. Good balance between leaf and plant size.

The accompanying colored photograph illustrates in top perspective view the overall appearance of the new cultivar, showing the colors as true as it is reasonably possible to obtain in a colored reproduction of this type. The photograph was taken in December 1988.

The following is a detailed description of my new begonia cultivar based on plants produced under commercial practices in Ashtabula, Ohio, under greenhouse conditions. Color references are made to the Royal Horticultural Society Colour Chart except where general color terms of ordinary dictionary significance are used.

PARENTAGE

A controlled cross between *B. tuber hybrida* Mikkelsen seedling 84-628-16 as seed parent and *B. socotrana* Mikkelsen seedling 85-1016-3 as pollen parent.

PROPAGATION (A) Type cuttings: Leaf and stem cuttings. Leaf cuttings root in 18 days at 21° C. in summer and 24 days at 21° C. in winter. Stem cuttings 2–3 cm long root in 16 days at 21° C. in summer and 18 days at 21° C. in winter.

(B) Rooting habit: Abundant, fine, fibrous (both leaf and stem cuttings).

(C) Time for shoot development: For leaf cuttings, 10 weeks in summer to 13 weeks in winter to obtain shoots 4 to 5 cm long in length; for stem cuttings, 5 weeks in summer to 6 weeks in winter produce shoots 5–6 cm long.

PLANT DESCRIPTION (A) Form: Semi-spreading habit, strong stems that can hold the large flowers without breaking; herbaceous, vigorous, suitable for 25 cm hanging basket production. Flowers cover the mounded plant in a hanging basket.

(B) Habit of growth: Dense habit without opening between leaves. Good basal branching; usually vegetative shoots are formed at the basal nodes and flower shoots at the higher nodes.

(C) Foliage: Leaves simple, alternate, borne on strong petioles 5 to 6 mm in diameter on mature leaves; there is a reddish cast on all aged leaf petioles.

(1) *Size.*—Can vary greatly with leaf position on plant, number of shoots per plant, and environment; 11 to 12 cm across and 14 to 15 cm long when mature.

(2) *Shape.*—Ovate to nearly orbicular with slightly overlapping lobes, slightly convex.

(3) *Texture.*—Leathery, glabrous.

(4) *Margin.*—Serrated.

(5) *Color.*—Young foliage: top side, between 200A and B; veinal area 143A; under side, 183C. Mature foliage: top side, 148A with veinal area 143B; under side, 176B with veinal area 143B.

(6) *Venation.*—Palmate; 6–7 major veins.

FLOWERING DESCRIPTION (A) Flowering habits: Flowering in racemes, usually 3 flowers per raceme with many racemes in bloom at one time; flowering continuous more or less indefinitely.

(B) Natural flowering season: Will flower year around without controlling day length. Plants will flower earlier and more abundantly if subjected to a reduced day length of 12 hours for 2–3 weeks when day lengths are longer than 12 hours.

(C) Flower buds: 20 mm long and 30 mm wide just before opening, tepals are entire around margins; color 43A just before opening and 43C when immature.

(D) Flowers borne: On strong pendulous peduncles that are reddish in color and 3 to 4 mm in diameter.

(E) Quantity: Average of 3 flowers per peduncle, opening in sequence as raceme develops. Total number of flowers will vary with number of flowering shoots per plant.

(F) Tepals:

(1) *Shape.*—Outer, almost rounded; inner, more heart shaped.

(2) *Color.*—Top side in winter when opening between 43A and 43B, fading to between 44C and 44D.

(3) *Number of tepals.*—More than 20.

(4) *Size of tepals.*—Outer, 45 to 50 mm wide, 30 to 35 mm long; inner, 30 mm wide, 25 mm long.

(5) *Flower size.*—7 cm in diameter; however, environment can affect size.

(G) Reproductive organs:

(1) *Stamens.*—None as plant is fully double with anthers appearing as petals.

(2) *Pistels.*—(a) Stigma shape: curled, color gold. (b) Style color: greenish-purple. (c) Ovaries: 3 in number, 10–15 mm in diameter, winged, reddish-green in color.

DISEASE RESISTANCE

Desiré has shown resistance to powdery mildew.

I claim:

1. A new and distinct cultivar of Begonia plant named Desiré, as illustrated and described.

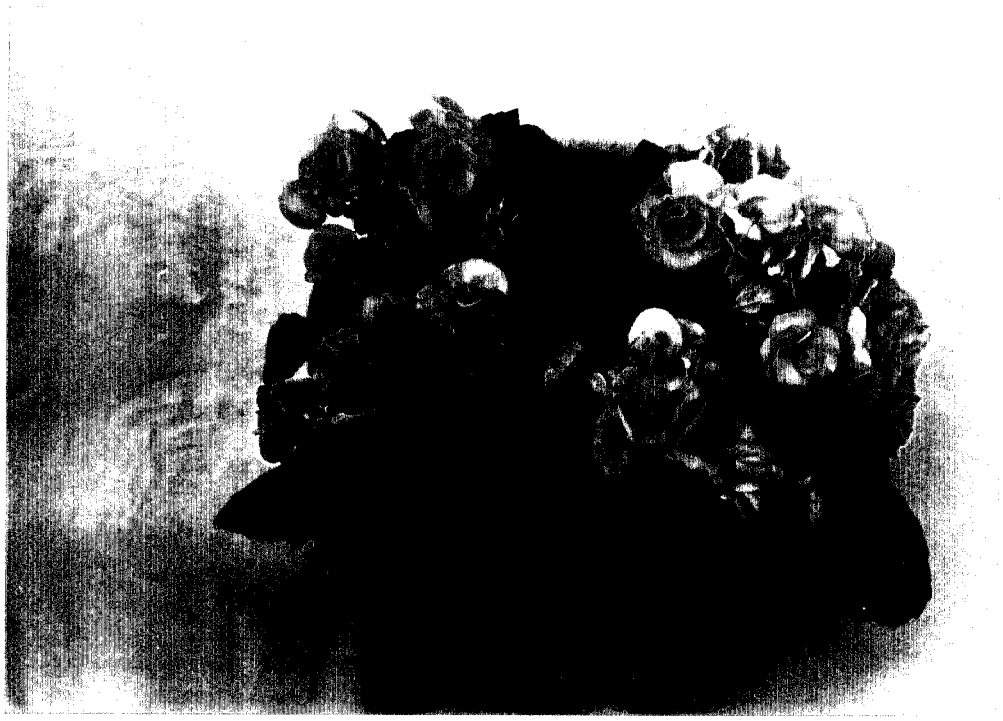

* * * * *